United States Patent [19]
Pigerol et al.

[11] 3,988,472
[45] Oct. 26, 1976

[54] TRI-N-PROPYLACETIC ACID DERIVATIVES FOR THERAPEUTIC USE

[75] Inventors: Charles Pigerol, St. Ouen; Pierre Luc Eymard, Fontaine, both of France

[73] Assignee: Labaz, Paris, France

[22] Filed: Nov. 10, 1975

[21] Appl. No.: 630,132

Related U.S. Application Data

[63] Continuation of Ser. No. 426,730, Dec. 13, 1973, abandoned.

[30] Foreign Application Priority Data

Dec. 11, 1972 France .............................. 72.43946

[52] U.S. Cl. ................................ 424/320; 424/317

[51] Int. Cl.² ....................................... A61K 31/16
[58] Field of Search ........................... 426/320, 317

[56] References Cited
OTHER PUBLICATIONS

Chem. Abst., vol. 51 – Subj. Index J–Z, pp. 2510s–2511s & 8693b (1957).

Primary Examiner—Stanley J. Friedman
Attorney, Agent, or Firm—Mason, Kolehmainen, Rathburn & Wyss

[57] ABSTRACT

Tri-n-propylacetamide and tri-n-propylacetic acid salts are useful in the treatment of pathological variations of mood and as anticonvulsants and tranquillizers.

3 Claims, No Drawings

TRI-N-PROPYLACETIC ACID DERIVATIVES FOR THERAPEUTIC USE

This is a continuation of application Ser. No. 426,730, filed Dec. 13, 1973, now abandoned.

This invention relates to tri-n-propylacetic acid derivatives for use in the treatment of pathological variations of mood, the said derivatives corresponding to the general formula:

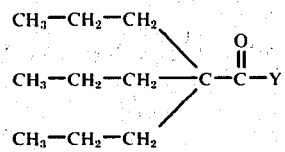

in which Y represents the group $NH_2$ or the group OM wherein M represents an alkali metal such as Li, Na or K.

These compounds may all be prepared by known processes such as the following:

a. when Y represents the group $NH_2$, tri-n-propylacetonitrile is gently hydrolysed in an acid medium, preferably sulphuric acid, as described in J. Amer. Chem. Soc. 70, 3091 (1948).

b. when Y represents the group OM, a base of the formula

MOH in which M has the values given above, is reacted with tri-n-propylacetic acid.

Another object of the invention is, therefore, the process of preparation of the compounds of the above general formula.

The invention also relates to pharmaceutical or veterinary compositions containing as active principle at least one compound of the above general formula in association with an appropriate pharmaceutical carrier.

Pharmacological trials carried out on experimental animals have shown that the compounds of the general formula possess properties which are of considerable value in the treatment of pathological conditions due to disturbances of the central nervous system and disorders relating to the field of neuropsychiatry. These pharmacological trials, which will be described in detail, have revealed that the compounds of the general formula can act as anticonvulsants, regulators of the central nervous system, tranquillizers and potentiators of central nervous system depressants.

In the course of further trials of the compounds of the invention as regulators of the central nervous system, it was unexpectedly discovered that the said compounds exert a particularly valuable curative effect upon pathological variations of mood. More especially, the compounds of the invention can constitute extremely useful agents for disinhibiting patients suffering from the severe listlessness or inability to communicate which may be referred to as apragmatism and which is found in such cases as, for example, certain types of schizophrenia.

It is, therefore, another object of the invention to provide a method of treating pathological variations of mood.

The derivatives defined by the above general formula are all known compounds inasmuch as they are covered by the general formula of British Pat. No. 760,114 relating to substances capable of reducing the level of cholesterol in the blood. Furthermore, tri-n-propylacetamide is specifically mentioned in British Pat. No. 469,921 in which it is presented as mildly spasmolytic and in Arch. fur Experim. Pathologie und Pharmakologie, 186 (July/Sept.) 1937 in which K. Junkmann describes it as a weak spasmolytic and somewhat stronger as a soporific. Apart from the fact that the information given in these two publications as regards tri-n-propylacetamide is not very precise with respect to dosage and experimental criteria, there is nothing in either text which could even remotely suggest the particular activities which, in the light of the present invention, can be attributed to the compounds of the general formula.

With particular regard to the activities which can be attributed to the compounds of the general formula as a result of the pharmacological trials referred to above and which will be described in detail, it should be noted that the use of the neuroleptic and anti-depressant agents known so far is accompanied by undesirable side-effects, such as, for example, extrapyramidal disturbances with the neuroleptics and complete reversals of mood with both types of agent. The compounds of the invention do not present these disadvantages. It has, in fact, been observed that they exert their effect at doses considerably lower than those required to provoke disturbances of behaviour.

In the field of diseases requiring anticonvulsant therapy and, in particular, epilepsy, there are numerous drugs of undeniable efficacy. However, these substances frequently cause undesirable side-effects, such as difficulty in fixing the attention, as well as biological disorders of which the most serious are haematological. Furthermore, certain well-known anticonvulsant agents are toxic at relatively low doses, while others are only useful for the treatment of one single type of epilepsy. The compounds of the invention do not present these disadvantages since they are relatively non-toxic and at the same time present a very wide range of properties which are likely to render them useful in the treatment of an extremely broad variety of convulsive states.

From the point of view of tranquillizing activity, the compounds of the invention are not put forward as possessing tranquillizing properties which are superior to those of the best agents so far known. However, it should be noted that the compounds of the invention, while being endowed with an appreciable tranquillizing action, also present a wide variety of neurotropic properties exceeding those of existing tranquillizers.

Finally, it should be emphasized that quite unexpectedly the compounds of the invention, as mentioned above, have been found to possess properties likely to render them extremely valuable in the treatment of pathological variations of mood and in particular in the treatment of severe apragmatism.

The following is an account of the pharmacological trials which have been undertaken with a view to determining the toxicity of the compounds of the invention and the presence of the various properties which, taken together, are capable of rendering the said compounds useful as anticonvulsants, regulators of the central nervous system, myorelaxants, tranquillizers and potentiators of central nervous system depressants.

1. Acute toxicity

The $LD_{50}$ was determined on the mouse by intraperitonel route using the technique of KARBER and BEHRENS. The results obtained for the preferred compounds of the invention were as follows:

| Compound | $LD_{50}$ in mg/kg |
|---|---|
| Sodium tri-n-propylacetate | 327 |
| Tri-n-propylacetamide | 340 | which corresponds to doses of 20 to 80 times the daily therapeutic doses of the compounds in question.

2. Neurotoxicity

The test used was that known as the rota rod test (BOISSIER - Therapie 1958, XIII, pp. 1074–1118). This test aims at enabling the animals' ability to coordinate their movements to be evaluated. It is carried out on batches of 10 mice each weighing about 25 g. The compound to be tested is administered by intraperitoneal route to the animals of each batch so that each batch receives a higher dose than that given to the preceding batch. Thirty minutes after administration, the mice are placed for two minutes on a wooden roller of 4.8 cm diameter which turns at the rate of 4 revolutions per minute. The roller has a rough surface to prevent the animals from slipping.

By this means, the neurotoxic dose 50 (NTD 50) can be determined, i.e. the dose of the compound with which one half of the animals can no longer stay on the roller during the period of time fixed as the reference period.

The results obtained with the preferred compounds of the invention were as follows:

| Compound | $NTD_{50}$ in mg/kg |
|---|---|
| Sodium tri-n-propylacetate | 120 |
| Tri-n-propylacetamide | 68 |

The value of this test is twofold. Failure on the part of the animals gives a very early indication of the slightest damage to the neuromuscular functions which cannot be discerned by any other means. Secondly, this test serves as an element of comparison for drawing up index figures involving the results obtained with other behaviour tests.

3. Anticonvulsant Action

The anticonvulsant action was first studied by the method involving a pentylenetetrazol-induced seizure and then by the maximum electroshock seizure technique.

a. Pentylenetetrazol-induced seizure

The purpose of this test which is carried out on mice is to determine whether the compounds of the invention, when given preventively by intraperitoneal route, are capable at certain doses of protecting some of the animals against the epileptic seizure produced by an adequate and predetermined dose of pentylenetetrazol which would be 100% fatal in the absence of the compound. The test was carried out on batches of 10 male OF 1 mice weighing about 25 g. Each batch of animals received an intraperitoneal dose of the compound to be studied so that each batch received a higher dose than the preceding batch. Seven-and-a-half minutes after administration, the animals were each given 125 mg/kg of pentylenetetrazol by intraperitoneal route. The experiment was repeated 15 minutes, 30 minutes, 45 minutes and 60 minutes after administration of the compound under study and the number of deaths was noted 3 hours after administration of the pentylenetetrazol. From these findings, the effective dose 50 or $ED_{50}$ was calculated by the method described by LITCHFIELD and WILCOXON in J. Pharmacol. 1938, 2 pp. 192–216.

The results obtained with the preferred compounds of the invention are given in the following Table

TABLE I

| Compound | Time after administration | | | | |
|---|---|---|---|---|---|
| | 7 min. 30 sec. | 15 min. | 30 min. | 45 min. | 60 min. |
| Sodium tri-n-propylacetate $ED_{50}$ in mg/kg | 78 | 66 | 110 | | |
| Tri-n-propylacetamide $ED_{50}$ in mg/kg | | 10 | 38 | 56 | 70 |

As regards sodium tri-n-propylacetate, there was no longer any relationship between activity and the dose administered after 45 minutes and 60 minutes because at these times the moment of peak activity of the compound had been considerably exceeded and elimination was already fairly well advanced. For the tri-n-propylacetamide it was not possible to calculate a $ED_{50}$ after 7 minutes 30 seconds as the action of the compound was not discernable at that time.

The efficacy index of the compounds was also calculated by comparing the $ED_{50}$ with the dose required to obtain a hypnotic effect in 50% of the animals. This latter value is indicated by the symbol $HD_{50}$ or hypnotic dose 50 and the efficacy index by the fraction:

$$\frac{HD_{50}}{ED_{50}}$$

The efficacy indices obtained for the preferred compounds as well as for phenobarbital were as follows:

| | |
|---|---|
| Sodium tri-n-propylacetate | 1.8 |
| Tri-n-propylacetamide | 9 |
| Phenobarbital | 3.3 |

These figures show that tri-n-propylacetamide is much more advantageous than phenobarbital whereas sodium tri-n-propylacetate is as sedative as phenobarbital. However, sodium tri-n-propylacetate, while presenting an appreciable degree of activity as compared with its $HD_{50}$, does not have the well-known disadvantages of the barbiturates.

b. Maximum electroshock seizure

This seizure is characterized in the mouse by extension of the back paws for 5 to 10 seconds. The extension is similar to that observed during the tonicoclonic seizures provoked by chemical convulsants such as pentylenetetrazol or strychnine.

The test was carried out on batches of 10 mice of the OF 1 strain weighing about 22 g. Various doses of the compound to be tested were administered by intraperitoneal route so that each batch of animals received a higher dose than that given to the preceding batch.

Fifteen minutes later, each animal received an electric shock of twice threshold intensity (about 60 volts). The number of tonic seizures was noted and the $ED_{50}$ was calculated, i.e. the dose of the compound under study required to protect 50% of the animals against tonic seizures.

The following results were obtained for the preferred compounds of the invention and for phenobarbital:

| Compound | $ED_{50}$ in mg/kg |
|---|---|
| Sodium tri-n-propylacetate | 130 |
| Tri-n-propylacetamide | 82 |
| Phenobarbital | 78 |

As in the case of the pentylenetetrazol-induced seizure test, the efficacy index:

$$\frac{HD_{50}}{ED_{50}}$$

was calculated and the following results recorded:

| Sodium tri-n-propylacetate | 1.0 |
|---|---|
| Tri-n-propylacetamide | 1.3 |
| Phenobarbital | 1.3 |

These figures show that tri-n-propylacetamide, which does not have the disadvantages of the barbiturates, possesses a degree of activity which is comparable to that of phenobarbital. It can also be seen that sodium tri-n-propylacetate, although less active than phenobarbital, exerts its effect at a dose well below its $LD_{50}$.

4. Myorelaxant properties

The myorelaxant properties of the compounds of the invention were determined by the traction test described by COURVOISIER (Psychotropic Drugs, Milan 1957; pp. 373–391) and at the same time verifying the anti-strychnine properties of these compounds.

a. Traction Test

This test enables sense of balance as well as muscular tonus and strength to be evaluated.

The test is carried out on groups of 10 male mice of the OF 1 strain weighing about 25 g. It consists in suspending the mice by the front paws to a horizontally stretched wire. Note is first taken of the time required by a group of control animals to effect recovery i.e. to place at least one of their back paws on the wire. Each batch of animals is then given an intraperitoneal dose of the compound to be studied so that each batch receives a higher dose than the preceding batch. Note is then taken of the number of animals which have lost the traction reflex 30 minutes after administration of the compound and the $ED_{50}$ is calculated i.e. the dose of the compound understudy which causes loss of the reflex in 50% of the animals.

In order to obtain an activity index figure, the rota rod test described above was also performed using for comparison two known myorelaxants, namely diazepam and mephenesin.

The following results were recorded:

| | Tri-n-propyl-acetamide | Diazepam | Mephenesin |
|---|---|---|---|
| $NTD_{50}$ in the rota rod test in mg/kg | 68 | 3 | 100 |
| $ED_{50}$ in the traction test in mg/kg | 45 | 2.75 | 250 |
| Activity index: $\frac{NTD_{50}}{ED_{50}}$ | 1.5 | 1.1 | 0.4 |

These figures show a very favourable activity index for tri-n-propylacetamide as compared with the activity indices of two known myorelaxants. It is seen, in fact, in the case of tri-n-propylacetamide, that the myorelaxant dose is much further removed from the neurotoxic dose than in the case of the other two substances.

b. Antagonism to strychnine

Male mice of the OF 1 strain, weighing 22 to 24 g were treated by intraperitoneal route with a compound of the invention.

Thirty minutes later, the animals were given a subcutaneous dose of 1.5 mg/kg of an aqueous solution of strychnine sulphate.

The number of deaths occurring during the two hours following administration of the strychnine sulphate was noted and the $ED_{50}$ calculated. The $ED_{50}$ recorded for tri-n-propylacetamide was 65 mg/kg.

5. Hypnotic properties

The hypnotic properties of the compounds of the invention were demonstrated by studying posture reflex.

Male mice of the OF 1 strain, weighing about 25 g, were divided into batches of 10. The animals of each batch were given an intraperitoneal dose of the compound to be studied so that each batch received a higher dose than the preceding batch.

The numbers of animals which lost the reflex at various times after administration were noted.

In this way, the $HD_{50}$ at different times after administration was determined i.e. the dose of the compound under study which caused 50% of the animals to lose the posture reflex at a given time after administration.

The results recorded are given in the following Table:

TABLE II

| Compound | Time after administration | | | |
|---|---|---|---|---|
| | 15 min. | 30 min. | 45 min. | 60 min. |
| Sodium tri-n-propylacetate $HD_{50}$ in mg/kg | 120 | 130 | 150 | 200 |
| Tri-n-propylacetamide $HD_{50}$ in mg/kg | 90 | 110 | 110 | 120 |

6. Tranquillizing properties

The tranquillizing properties of the compounds of the invention were demonstrated by the chimney test, the evasion test and the hole-board test described by BOISSIER in Med. Exp. 1960, 3, pp. 81–84, Therapie 1965, XX, pp. 895–905 and Therapie, 1964, XIX, pp. 571–589 respectively.

a. Chimney test

This test enables two groups of factors to be evaluated namely neuromuscular factors (muscular strength, agility, coordination of movements) and psychological factors (curiosity, fright, flight instinct).

It was carried out on batches of 10 mice weighing about 25 g each. The compound to be studied was given to each batch by intraperitoneal route so that each batch received a higher dose than the preceding batch. The mice were placed, one after another, head first in a test-tube 30 cm long and calibrated in accordance with the size of the mouse so that by moving backwards the animal could get out of the tube in less than 30 seconds. The number of animals which were unable to do this was noted.

In this way, the $ED_{50}$ could be determined i.e. the dose of the compound at which 50% of the animals failed to get out of the test-tube within the 30-second period.

The following results were obtained with the preferred compounds of the invention:

| Compound | $ED_{50}$ in mg/kg |
|---|---|
| Sodium tri-n-propylacetate | 72 |
| Tri-n-propylacetamide | 32 |

These tranquillizing effects were obtained at only half the doses required to modify neuromuscular functions in the rota rod test.

b. Evasion test

This test enables the exploring capacities of mice to be studied. A parallelepipedic lidless plywood box is used which contains an inclined plane, also of plywood, covered with a fine mesh. A horizontal datum line is marked on the inclined plane 2 cm below the point at which the plane bears on the box edge. The whole device is placed in an artificially lit room away from all shrill noise. Any crossing, in an upward direction, by a mouse of the datum line is termed an "exit".

The test was carried out on batches of 28 mice weighing about 22 g. The animals of each batch received an intraperitoneal dose of the compound to be studied so that each batch received a higher dose than the preceding batch.

Thirty minutes after administration of the compound, the animals were placed in the box by batches and kept at the bottom for 10 seconds by a movable board. The average length of time after which the first exit occurred was noted as well as the total number of exits per batch every minute for 5 minutes. These same details were also recorded for a control batch which had not received the compound. The following results were obtained with the preferred compounds of the invention:

TABLE III

| Compound | Total number of exits per batch | | | | | Average time before first exit in seconds |
|---|---|---|---|---|---|---|
| | 1 min. | 2 min. | 3 min. | 4 min. | 5 min. | |
| Controls | 48 | 50 | 43 | 38 | 42 | 14 |
| Sodium tri-n-propyl acetate 50 mg/kg | 54 | 44 | 43 | 41 | 28 | 25 |
| Sodium tri-n-propyl acetate 75 mg/kg | 44 | 37 | 31 | 34 | 28 | 21 |
| Tri-n-propyl-acetamide mg/kg | 46 | 37 | 27 | 26 | 35 | 20 |

TABLE III-continued

| Compound | Total number of exits per batch | | | | | Average time before first exit in seconds |
|---|---|---|---|---|---|---|
| | 1 min. | 2 min. | 3 min. | 4 min. | 5 min. | |
| Controls | 48 | 50 | 43 | 38 | 42 | 14 |
| Tri-n-propyl-acetamide 50 mg/kg | 40 | 43 | 38 | 31 | 25 | 49 | c. Hole-board test

This test enables a quantitative evaluation to be made of the exploring capabilities of mice in relation to their curiosity. The material comprises a board 40 cm × 40 cm and 1.7 cm thick in which 16 holes, 3 cm in diameter, have been cut. The board is placed upon four legs sufficiently high (1.5 m) for the holes to appear bottomless to the animals. The experiment is carried out in as great a silence as possible.

The test was performed on batches of 10 male OF 1 mice weighing about 23 g. The animals of each batch were given an intraperitoneal dose of the compound to be tested so that each batch received a higher dose than the preceding batch. The control group did not receive any of the compound under study.

Thirty minutes after administration, each batch was placed in the middle of the board and the total number of holes explored by each batch was noted every minute for 5 minutes.

The results obtained with the preferred compounds of the invention are given in the following Table:

TABLE IV

| Compound | Total number of holes explored | | | | |
|---|---|---|---|---|---|
| | 1 min. | 2 min. | 3 min. | 4 min. | 5 min. |
| Controls | 32 | 35 | 32 | 43 | 33 |
| Sodium tri-n-propyl acetate 50 mg/kg | 15 | 13 | 14 | 19 | 17 |
| Sodium tri-n-propyl acetate 75 mg/kg | 2 | 6 | 3 | 1 | 7 |
| Tri-n-propyl-acetamide 10 mg/kg | 30 | 28 | 28 | 35 | 27 |
| Tri-n-propyl-acetamide 50 mg/kg | 8 | 10 | 4 | 6 | 12 |

The above results show that both sodium tri-n-propylacetate and tri-n-propylacetamide tend to reduce the animals' curiosity.

7. Neuroleptic properties

All the catalepsy tests carried out on the rat (crossing of homolateral paws, four corks test, parallel bars test) with the compounds of the invention gave negative results with doses just below the hypnotic doses.

8. Potentialization of central nervous system depressants

Tests were carried out in order to determine the potentializing effect of compounds of the invention on sodium pentobarbital and on neuroleptics.

a. Sodium pentobarbital

An intraperitoneal dose of 50 mg/kg of the compound to be studied was given to batches of 10 mice of the OF 1 strain weighing 22 to 24 g. Thirty minutes later, a dose of 30 mg/kg of sodium pentobarbital was given by the same route. Note was taken of the average time before the animals fell asleep as well as the average duration of the sleep. The combined action of the two substances thus administered was compared to that of 50 mg of the same compound given alone under the same circumstances and to that of 30 mg/kg of sodium pentobarbital also given alone under the same circumstances.

The following results were obtained with tri-n-propylacetamide:

TABLE V

| Compound | Average time before onset of sleep | Average duration of sleep |
|---|---|---|
| Tri-n-propylacetamide 50 mg/kg | No mice asleep | No mice asleep |
| Sodium pentobarbital 30 mg/kg | No mice asleep | No mice asleep |
| Tri-n-propylacetamide 50 mg/kg + Sodium pentobarbital 30 mg/kg | 4 min. 45 sec. | 1 min. 37 sec. | b. Potentialisation of neuroleptics

For this test batches of 10 mice of the OF 1 strain, weighing 22 to 24 g, were used. A dose of 5 mg/kg of chlorpromazine was given to one batch and a dose of 50 mg/kg of the compound to be studied was given to another. The results obtained were compared with those registered with two more batches both of which received a dose of 5 mg/kg of chlorpromazine. Thirty minutes later one of these latter batches received 10 mg/kg of the compound to be studied and the other 50 mg/kg. In all cases, administration was by the intraperitoneal route.

The following results were obtained with tri-n-propylacetamide as compound of the invention.

TABLE VI

| Compound | % of cataleptic animals |
|---|---|
| Tri-n-propylacetamide 50 mg/kg | No catalepsy |
| Chlorpromazine 5 mg/kg | No catalepsy |
| Tri-n-propylacetamide 10 mg/kg + Chlorpromazine 5 mg/kg | 40 |
| Tri-n-propylacetamide 50 mg/kg + Chlorpromazine 5 mg/kg | 100 |

9. Antireserpine action

The antidepressants antagonize or delay the sedative action of reserpine as measured by means of the occurrence of ptosis in the rat. An intraperitoneal dose of 50 mg/kg of the compound to be studied was administered to batches of 5 male rats of the CF 1 strain weighing about 300 g. Thirty minutes later, 5 mg/kg of reserpine was given by the same route. Ptosis was noted in relation to the length of time after injection of the reserpine and was measured on each eye in accordance with the following scale:
 0: eyelids open
 1: eyelids 1/4 closed
 2: eyelids 1/2 closed
 3: eyelids 3/4 closed
 4: eyelids completely closed Thus, for example, if an animal had a ptosis value of 1 for one eye and 2 for the other, it was given the score of 1.5.

The results obtained with tri-n-propylacetamide are as follows, each result representing the average of 10 evaluations (5 animals of which both eyes were examined):

| Compound | Ptosis | | | | |
|---|---|---|---|---|---|
|  | 1 h | 2 h | 3 h | 4 h | 6 h |
| Controls | 0.6 | 2.0 | 3.3 | 4.0 | 4.0 |
| Tri-n-propylacetamide 10 mg/kg | 0.2 | 2.6 | 3.6 | 3.8 | 4.0 |
| Tri-n-propylacetamide 20 mg/kg | 0 | 2.4 | 3.4 | 3.5 | 3.8 |
| Tri-n-propylacetamide 30 mg/kg | 0 | 0.8 | 2.3 | 3.2 | 4.0 |
| Tri-n-propylacetamide 40 mg/kg | 0 | 0.8 | 2.3 | 3.0 | 4.0 |

The therapeutic compositions of the invention may be presented in any form suitable for administration in human or veterinary medicine. The unit of administration may be in the form of, for example, a coated- or uncoated-tablet, a soft- or hard-gelatin capsule, an ampoule or syrup for oral administration, of a sterile solution for parenteral administration and of a suppository for rectal administration.

According to the type of administration unit chosen, the therapeutic compositions of the invention will be prepared by associating at least one of the compounds of formula I with an appropriate excipient, the latter being composed, for example, of at least one ingredient selected from amongst the following substances: talc, magnesium stearate, milk sugar, saccharose, carboxymethylcellulose, starches, kaolin, levilite, cocoa-butter.

The preparation of the compounds of the invention together with therapeutic compositions containing them are illustrated by the following non-limitative Examples.

EXAMPLE I

Preparation of tri-n-propylacetamide a. Preparation of tri-n-propylacetonitrile

In a 4-liter flask equipped with a dropping-funnel and a mechanical stirrer was placed a solution of 123 g (3 mol) of acetonitrile and 1410 g (11.4 mol) of n-propyl bromide in 520 g of toluene. The solution was heated, while being stirred, to 50° C after which a 90% suspension of 431 g of sodium amide in 775 g of toluene was slowly introduced over a period of 5 hours through the dropping-funnel, care being taken to maintain the temperature above 50° C. During this operation, it was observed that the reflux temperature rose from 50° C to 75° C. The flask which had contained the sodium amide suspension was then rinsed with 180 g of toluene. The reaction mixture was allowed to descend to room-temperature and stirring was maintained for 14 hours. The reaction mixture together with the rinsing liquid were gradually and carefully poured into iced water comprising 2000 g of purified water and 500 g of ice. The mixture was stirred for 30 minutes and the organic layer decanted off and washed three times with 1 liter of water after which the toluene was distilled off. The oily residue was distilled under reduced pressure (2 mm. Hg) and the distillation fraction was recovered which boiled between 68 and 70° C. In this way, 400 g of tri-n-propylacetonitrile were obtained which represented a yield of 80%.

b. Preparation of tri-n-propylacetamide

In a 2-liter flask an 80% aqueous solution of 550 g of sulphuric acid was placed. While stirring, 110 g (0.66 mol) of tri-n-propylacetonitrile were added over a period of 20 minutes and at room-temperature. The temperature of the reaction medium rose to 80° C after which it was brought up to 105°–110° C for 6 hours. The solution was then cooled to 10° C and slowly poured into iced water (1000 g of purified water and 200 g of ice.) A pasty precipitate gradually formed as the solution was added to the iced water. As soon as the operation was finished, the mixture was stirred for 15 minutes and the precipitate centrifuged out and taken up twice in 350 g of ethyl ether. The ethereal solution was first washed twice with 200 g of water containing 10% of sodium bicarbonate and then twice with 250 g of water. The mixture was dried for 24 hours over 125 g of anhydrous sodium sulphate after which the sodium sulphate was centrifuged out. The ether was then eliminated by means of a rotatory evaporator which provided an oil which crystallized into fine needles which were left under vacuum until a constant weight was obtained. By this means, 113 g of crude tri-n-propylacetamide were obtained which represents a yield of 92.6%. The crude product was then dissolved by heating in 150 g of petroleum ether. After dissolution, 1.15 g of CECA WSL black was added and the mixture refluxed for 30 minutes. The black was then filtered off while the mixture was still hot. The filtrate was cooled to −15° C for 3 hours after which the precipitate which formed was centrifuged out and dried for 24 hours in a drying-oven at 40° C under 20 mm. Hg vacuum. In this way, 98.5 g of pure tri-n-propylacetamide were obtained which represents a yield in pure product of 87.1%. M.P. 69° C.

EXAMPLE 2

Preparation of sodium tri-n-propylacetate a. Preparation of tri-n-propylacetic acid In a flask equipped with a dropping-funnel were placed 480 g of distilled dioxan followed by 80 g (0.432 mol) of tri-n-propylacetamide which was dissolved by stirring. For a period of 20 minutes a current of dry hydrochloric acid gas was passed through the dioxan solution at room-temperature, which represented a total of 100 g of hydrochloric acid gas. At the end of this operation, 88 g (0.86 mol) of freshly distilled butyl nitrile was slowly added over a period of 2 hours through the dropping-funnel. The temperature of the reaction medium rose from 31 to 43° C which necessitated cooling in a water-bath. The solution was then maintained for 2 hours at 85°–90° C. The dioxan was distilled off under a reduced pressure of 20 mm. Hg and a pasty residue obtained at room-temperature. This residue was dissolved in 290 g of a 10% aqueous solution of potassium hydroxide. The aqueous layer was decanted out and extracted twice with 75 g of ethyl ether. The potassium solution was acidified with 118 g of a 36% solution of hydrochloric acid (at 10/20° C) after which the oily phase was decanted out. The aqueous phase was extracted twice with 75 g of ethyl ether after which the oily phase and the ethereal extracts were placed together. The ethereal solution was washed twice with 100 g of water and dried for 24 hours over 100 g of anhydrous sodium sulphate. The sodium sulphate was then centrifuged out. The ethyl ether was distilled off under atmospheric pressure and the residue recuperated under 7 mm Hg. The fraction obtained boiled at 126° to 128° C and crystallized rapidly. In this way, 61 g of crude tri-n-propylacetic acid were obtained, which represents a yield of 76%. The crude product was then dissolved by heating in 75 g of ethyl ether. The ethereal solution was filtered while hot and the filtrate left at a temperature of −30° C for 4 hours. The precipitate which formed was centrifuged out and dried in a desiccator under a reduced pressure of 20 mm Hg for 6 hours. By this means, 46 g of pure tri-n-propylacetic acid were obtained which represents a yield in pure product of 75.4% and a total yield of 57.3%. M.P. 67° C.

b. Preparation of sodium tri-n-propylacetate

In a flask equipped with a dropping-funnel and a mechanical strirrer were placed 30 g (0.161 mol) of pure tri-n-propylacetic acid prepared as described above and 75 g of toluene. The mixture was stirred until dissolution after which a hot solution of 6.45 g of sodium hydroxide in 30 g of methanol was added through the dropping-funnel. To the solution thus obtained was added 1 g of CECA WSL black after which the whole was refluxed for 1 hour while being stirred. The black was filtered off and the residual mixture was distilled by adding little-by-little through the dropping-funnel 88 g of toluene to prevent the mixture from forming a mass. Distillation was suspended when the temperature at the head of the column reached 105° C, after which the mixture was cooled to room-temperature. The precipitate which formed was centrifuged out and rinsed twice with 20 g of acetone. It was then dried in a rotatory evaporator at 80° C for 2 hours and then at 105° C under atmospheric pressure in a ventilated drying-oven for 4 hours. In this way, 30 g of sodium tri-n-propylacetate were obtained which represents a yield of 89.5%.

EXAMPLE 3

Soft-gelatin capsules corresponding to the following formulation were prepared by known pharmaceutical techniques:

| Ingredient | mg per capsule |
| --- | --- |
| Tri-n-propylacetamide | 150 |
| Talc | 15 |
| Magnesium stearate | 2 |
|  | 167 |

Dosage

The daily dosage of the compounds of this application is 50 to 500 mgs. and preferably 100 to 300 mgs. by the oral route.

We claim:

1. A method of inducing tranquillizing, disinhibiting and antidepressant effects in a subject needing such treatment, said method comprising administering a dosage ranging from 50 to 500 mgs. per day of tri-n-propylacetamide to said subject.

2. The method according to claim 1 wherein the dosage is 100 to 300 mgs. by the oral route.

3. A method according to claim 1 for the treatment of apragmatism.

* * * * *

FO-1050
(5/69)

UNITED STATES PATENT OFFICE
CERTIFICATE OF CORRECTION

Patent No. 3,988,472                Dated October 26, 1976

Inventor(s) Charles Pigerol and Pierre Luc Eymard

It is certified that error appears in the above-identified patent and that said Letters Patent are hereby corrected as shown below:

Column 7, last line, before "mg/kg" insert -- 10 --.

Signed and Sealed this

First Day of February 1977

[SEAL]

Attest:

RUTH C. MASON
Attesting Officer

C. MARSHALL DANN
Commissioner of Patents and Trademarks